United States Patent [19]
Darke et al.

[11] Patent Number: 5,618,685
[45] Date of Patent: Apr. 8, 1997

[54] ACTIVATION OF HERPES SIMPLEX VIRUS PROTEASE BY KOSMOTROPES

[75] Inventors: Paul L. Darke, Blue Bell; Dawn L. Hall, Spring City; Lawrence C. Kuo, Solebury, all of Pa.

[73] Assignee: Merck & Co., Inc., Rahway, N.J.

[21] Appl. No.: 417,624

[22] Filed: Apr. 6, 1995

[51] Int. Cl.$^6$ .............................. C12Q 1/37; C12Q 1/34; C12Q 1/02; A61K 38/00
[52] U.S. Cl. .............................. 435/23; 435/18; 435/24; 435/34; 435/5; 435/4; 435/29; 435/235.1; 530/300; 530/328; 530/329
[58] Field of Search ..................... 435/18, 23, 4, 435/34, 5, 24, 29, 235.1; 530/329, 328, 300

[56] References Cited

U.S. PATENT DOCUMENTS

| | | | |
|---|---|---|---|
| 4,618,578 | 10/1986 | Burke et al. | 435/23 |
| 5,066,783 | 11/1991 | Cohen et al. | 435/23 |
| 5,122,449 | 6/1992 | Gilbert et al. | 435/5 |
| 5,151,267 | 9/1992 | Babiuk et al. | 435/23 |
| 5,208,031 | 5/1993 | Kelly | 435/23 |
| 5,324,664 | 6/1994 | Nunberg et al. | 435/69.1 |

FOREIGN PATENT DOCUMENTS 0514830  11/1992  European Pat. Off. .

OTHER PUBLICATIONS

Collins, K.D. et al. Quarterly Review of Biophysics 18, 4 (1985) pp. 323–422.
Plotch, S.J. et al. Cell 23 (1981) pp. 847–858.
Chung, T.D.Y. et al. Proc. Natl. Acad. Sci. USA 91 (1994) pp. 2372–2376.
Darke, P.L. et al. Activation of the Herpes Simplex Virus – 1 Protease, 1994, pp. 1–20.

*Primary Examiner*—John Kight
*Assistant Examiner*—Louise Leary
*Attorney, Agent, or Firm*—Joanne M. Giesser; Jack L. Tribble

[57] ABSTRACT

Native Herpes Simplex Virus type 1 (HSV type 1) protease has a rather low activity. It has been found however, that the presence of a kosmotropic anion can increase the activity of the protease over 10-fold. This has many advantages, as now assays for protease activity may be run in very small (micromolar and less) amounts of reagents and substrates, and the assays can be run quickly. Activate HSV-1 protease represents a conformational change from native protease.

16 Claims, 2 Drawing Sheets

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
      ( A ) LENGTH: 14 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:1:

```
His  Thr  Tyr  Leu  Gln  Ala  Ser  Glu  Lys  Phe  Lys  Met  Trp  Gly
 1                  5                        10
```

( 2 ) INFORMATION FOR SEQ ID NO:2:

( i ) SEQUENCE CHARACTERISTICS:
      ( A ) LENGTH: 13 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:2:

```
His  Thr  Tyr  Leu  Gln  Ala  Ser  Glu  Lys  Phe  Lys  Met  Trp
 1                  5                        10
```

-continued ( 2 ) INFORMATION FOR SEQ ID NO:3:

( i ) SEQUENCE CHARACTERISTICS:
( A ) LENGTH: 7 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:3:

Ser Glu Lys Phe Lys Met Trp
1 5

( 2 ) INFORMATION FOR SEQ ID NO:4:

( i ) SEQUENCE CHARACTERISTICS:
( A ) LENGTH: 8 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( x i ) SEQUENCE DESCRIPTION: SEQ ID NO:4:

Ser Glu Lys Phe Lys Met Trp Gly
1 5

ACTIVATION OF HERPES SIMPLEX VIRUS PROTEASE BY KOSMOTROPES

DESCRIPTION OF THE INVENTION

This invention relates to a method of increasing the activity of Herpes Simplex Virus protease by including kosmotropic anion in a reaction medium and to assays which involve the activated protease.

BACKGROUND OF THE INVENTION

Herpes Simplex Virus type 1 (HSV-1) protease must be catalytically active for successful nucleocapsid maturation, replication of the virus and infectivity of the virus. The proteases of HSV-1 and related herpes-group viruses are synthesized as precursor proteins (designated Pra) which undergo autoproteolytic processing during viral assembly to release a protease catalytic domain localized in the N-terminus of the precursor. In the case of HSV, the catalytic domain is within the N-terminal 247 amino acids of the 635 amino acid precursor protein. The mature processed form of the protease is a 27 kDa protein.

The only known protein substrates for the HSV protease are the viral protease precursor and the viral assembly protein known as ICP35 (Infected Cell Protein 35 or VP22a). Both ICP35 and the protease precursor are encoded by the $U_L26$ gene of HSV-1, with initiation of ICP35 translation occurring 306 codons after the initiation codon of the protease precursor, although the frequency in translation of ICP35 is approximately 10 times that of the precursor protease. (Liu, F. and Roizman, B. 1991, *J. Virol.* 65: 5149–5156, and Liu, F. and Roizman, B. 1991, *J. Virol.* 65: 206–212.) The reading frames for both proteins are the same, with the sequence of ICP35 identical to the C-terminus of the precursor protein.

The more abundant ICP35 is present in an immature form of the HSV capsids, known as B capsids, during capsid assembly within infected cell nuclei. The proteolytic conversion of ICP35 from the form found within the B capsids (ICP35 cd) to the shorter form found only within cell nuclei (ICP35 ef) is temporally linked with the conversion of B capsids to C capsids, which contain DNA. Thus, HSV protease action occurs within the cell nucleus and possibly within the viral capsid itself.

The mature form of the HSV-1 protease has been isolated following expression in *E. coli* and baculovirus systems. Inactivation with diisopropyl fluorophosphate was used to suggest the enzyme is a serine protease, but primary structure homology analyses have not revealed close relationships with well characterized groups of serine (or other) proteases. Peptides that represent cleavage sites within the natural protein substrates are cleaved at the bond between the characteristic Ala-Ser sequence found in protein substrates.

The $k_{cat}/K_M$ of the purified mature HSV protease was found to be only 38 $M^{-1}$ $s^{-1}$ using peptide substrates, and a $k_{cat}/K_M$ value of 36 $M^{-1}$ $s^{-1}$ has been reported using a fusion form of the enzyme with a similar assay condition, which includes 25% glycerol. These values are much lower than observed for other viral proteases such as rhinovirus 3C protease (1440 $M^{-1}$ $s^{-1}$) and HIV protease (13,000 $M^{-1}$ $s^{-1}$), and many orders of magnitude lower than other serine proteases such as chymotrypsin and thrombin ($10^7$ $M^{-1}$ $s^{-1}$). While it is conceivable that the comparatively low catalytic efficiency of the HSV protease observed in vitro may be sufficient to account for its essential physiological role in nucleocapsid assembly, the low activity prompts consideration that some factor might enhance catalytic efficiency. In any event it would be desirable to be able to have a more active form of the protease in order to better study its activity.

DETAILED DESCRIPTION OF THE INVENTION

This invention provides a method for increasing the activity of Herpes Simplex Viral type 1 (HSV-1) protease by including a kosmotropic anion in a reaction medium.

Another aspect of this invention is an improved assay for HSV-1 protease activity comprising preparing an aqueous reaction medium comprising the HSV-1 protease, a protease substrate, a kosmotropic anion, and optionally a substance suspected of altering HSV-1 activity and measuring the resultant protease activity. The presence of the kosmotropic anion allows this assay to be conducted in minutes, rather than the hours previously needed. Yet another aspect of this invention is an improved assay for HSV-1 protease which employs nanomolar quantities of enzyme using a reaction medium comprising kosmotropic anions.

A further aspect of this invention is the activated form of HSV-1 protease, formed when the protease is in a solvent comprising a kosmotropic anion.

The following definitions apply throughout the specification and claims:

Kosmotropic anion: an anion which has the property of increasing the specificity constant of HSV-1 protease by at least five times, and preferably at least ten times when it is in a reaction medium with the protease. A kosmotropic anion can be identified in the following assay. HSV-1 in an aqueous buffer at pH 7.5 cleaves the peptide substrate HTYLQASEKFKMWG-amide (SEQ.ID.NO.:1), with a specificity constant ($k_{cat}/K_M$) at pH 7.5 of 5.2 $M^{-1}$ $s^{-1}$; in the presence of a kosmotrope, but otherwise identical conditions, the specificity constant will be greater than 26 $M^{-1}s^{-1}$, and preferably greater than 52 $M^{-1}$ $s^{-1}$.

Activated HSV-1 protease: Herpes Simplex Virus protease in the conformational form which is distinct from the native form (HSV-1 protease is in an aqueous solution in the absence of a kosmotropic anion) and is identical to that which it assumes when in a reaction medium which also contains a kosmotropic anion.

$k_{cat}$: the observed catalytic rate constant of the enzyme-catalyzed reaction.

$K_M$: the Michaelis constant for enzyme interaction with substrate.

Specificity constant ($k_{cat}/K_M$): the apparent second-order rate constant for catalysis.

Figure 1A:
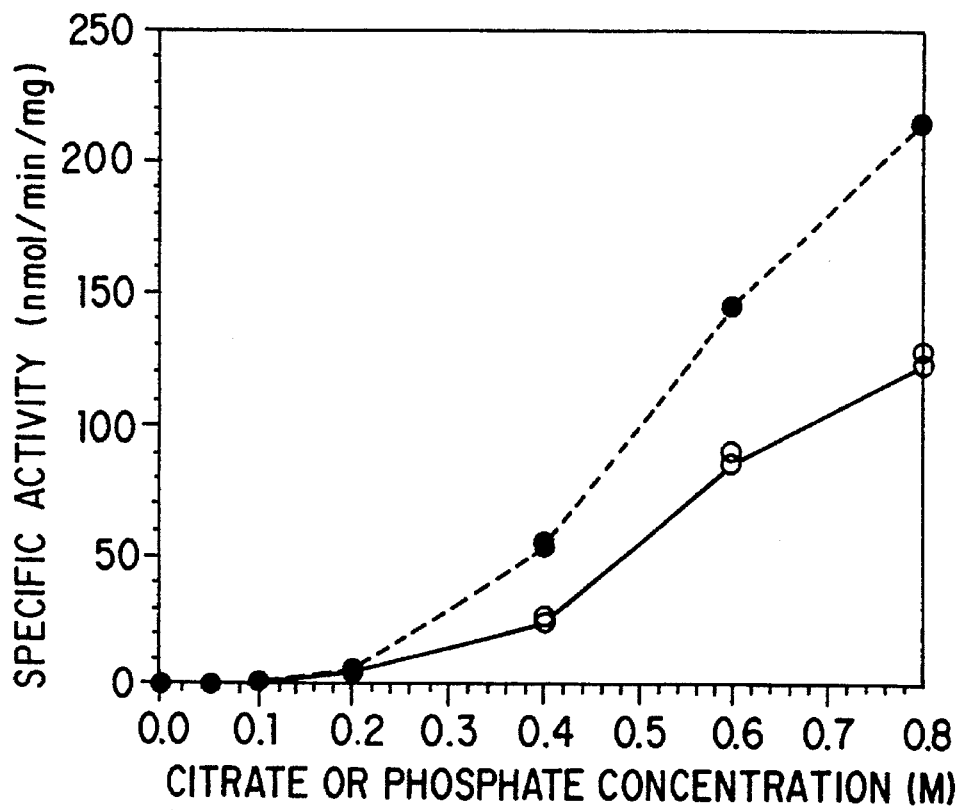
FIG. 1 is a graph showing the relative activity of HSV-1 protease as a function of sodium citrate or sodium phosphate concentration. HSV-1 protease activity at 37° C. was measured with the peptide HTYLQASEKFKMW-amide (SEQ.ID.NO.:2). Results for citrate are depicted using solid symbols and dotted line; those for phosphate are open symbols and solid line.

A kosmotrope is a substance (such as a solvent, and anion or a salt) which changes the solvent properties of water in a way which enhances the hydration of proteins. Kosmotropes are known (Collins et al., 1985, *Quart. Rev. Biophysics* 18: 323–422, which is hereby incorporated by reference). In the context of this invention, it has been found that kosmotropic anions increase the activity of HSV-1 protease by at least five-fold, and in preferred embodiments of this invention at least about ten-fold, and in certain cases, even in excess of 100-fold. Preferred kosmotropic anions in accordance with this invention are multivalent anions such as sulfate, succinate, phosphate, citrate, isocitrate and cis-aconitate, especially citrate and phosphate.

The presence of a kosmotropic anion has numerous beneficial effects, all of which comprise "activation" of the HSV-1 protease. First, the catalytic efficiency of the mature HSV-1 protease for cleavage of peptide substrates surprisingly increases. In addition, the susceptibility of the HSV-1 protease to proteolysis by trypsin is decreased in the presence of kosmotropic anions. Thus, further aspects of this invention include methods of decreasing the susceptibility of HSV-1 protease to trypsin proteolysis by including a kosmotropic anion in the reaction medium.

The extent of HSV-1 protease activation by various kosmotropic anions was shown to correlate with the Hofmeister series, with inhibition observed for $Br^-$ and $I^-$, little effect by $Cl^-$, some activation by $F^-$, and strong activation observed with multivalent anions such as sulfate, phosphate, citrate and isocitrate. Indeed, the activation data described here have the characteristic Hofmeister effect attributes: The effects become apparent at moderate concentrations, 0.01 to 1M; the effects are dominated by anions; and there is a sign inversion of effect at about NaCl. For example, an 860-fold increase of the protease activity ($k_{cat}/K_M$=4500 $M^{-1} s^{-1}$) was observed in the presence of 0.8M sodium citrate. Similarly, the presence of 0.8M sodium phosphate activates the catalytic efficiency by 420-fold ($k_{cat}/K_M$=2200 $M^{-1} s^{-1}$). Thus, in accordance with this invention, the preferred concentration of a kosmotropic anion in a reaction medium should range from about 0.01 to 1 molar; preferably about 0.5 to 1 molar, and particularly about 0.8 molar.

While not wishing to be bound be theory, it appears that the kosmotrope activation of HSV-1 protease is due to a conformational change of the protein. Kosmotropic anions may induce a more active conformation of the catalytic domain of the mature form of the enzyme. Thus, another aspect of this invention is the activated HSV-1 protease, i.e. in the conformational form the protease takes when in a reaction medium which includes kosmotropic anion. A particular embodiment of this invention is HSV-1 protease in its activated form, and free from host cell proteins.

Activation was observed, albeit to a lesser extent, with the multiply-hydroxylated alcohols, such as glycerol and sorbitol, as well as the anionic kosmotropes of this invention. Other solvents of more hydrophobic character, such as ethanol and dimethyl formamide, are strongly inactivating, even at 2% concentration. However, inhibition by these solvents can be overcome by addition of a kosmotropic anion of this invention. For example, while 2% DMSO reduced the HSV protease activity 37%, it only reduced activity 8% with 0.8M sodium citrate (a kosmotropic anion according to this invention) present. Thus another aspect of this invention is restoring activity to HSV protease which is in the presence of an inactivating substance by including a kosmotropic anion.

Figure 1B:
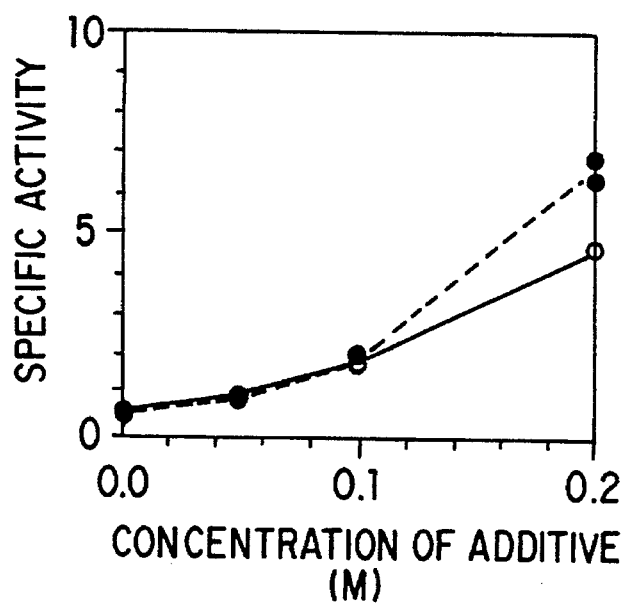

The anion activation data reported herein for the HSV protease are not characteristic of a site-specific binding event, as no saturation of the activation was observed (FIG. 1). In addition, a site-specific activation would be expected to display chemical structure correlations, but surprisingly, phosphate, citrate and isocitrate exhibited similar effects upon activity.

Figure 2:
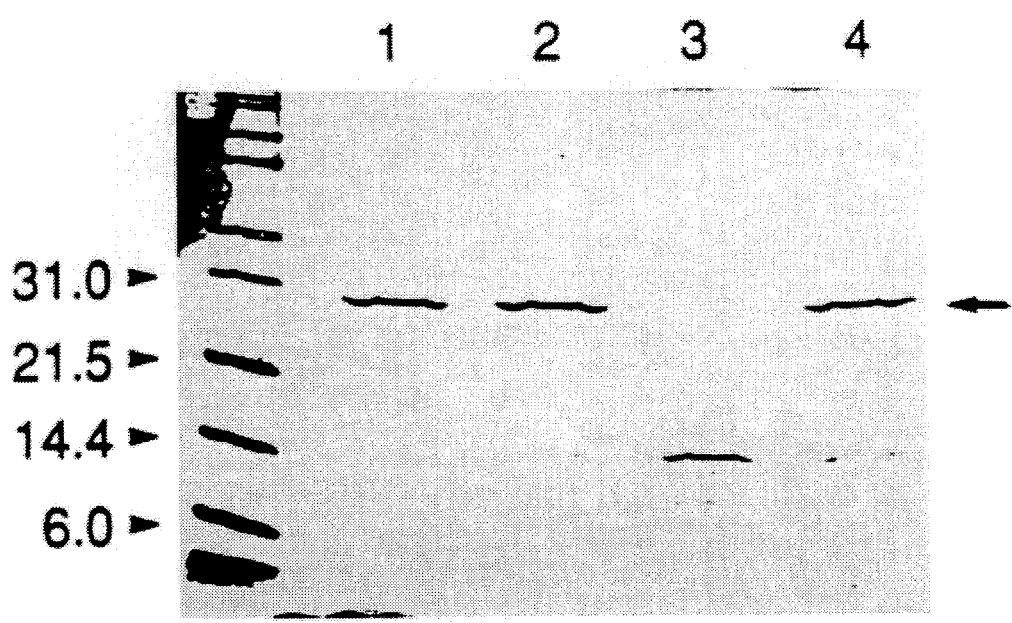
FIG. 2 is a photograph of a gel demonstrating the susceptibility of HSV-1 protease to trypsin proteolysis in the presence of sodium citrate. HSV-1 protease was incubated for 60 minutes at 37° C. with or without trypsin, either with or without 0.8M sodium citrate present, as described in Example 3. Samples were analyzed with SDS-PAGE (16% gels) and stained with Coomassie brilliant blue. Lanes 1 and 2, no trypsin added; lanes 3 and 4, trypsin added at 0.1 mg/ml. Lanes 1 and 3, no citrate added; lanes 2 and 4, sodium citrate present at 0.8M during incubation. The arrow on the right indicates the position of 27 kDa, undigested HSV-1 protease. Molecular weight markers are in the leftmost lane, with the corresponding molecular weights marked in kDa.

A comparison of the kcat and KM values for the substrate HTYLQASEKFKMW-amide (SEQ.ID.NO.:2) using different sodium citrate concentrations revealed that the kinetic parameter most changed by the kosmotropic anions is the $K_M$, such that 1.32 and 0.016 mM were obtained as $K_M$ values for 0.2M and 0.8M citrate, respectively. While not wishing to be bound by theory, it appears that since kosmotropes are also solutes which produce "salting-out" and aggregation effects for some proteins, it is conceivable that the lowering of $K_M$ observed here is a result of anion destabilization of the peptide substrate free in solution, producing a relative stabilization of the enzyme-substrate complex and a lowering of the observed $K_M$. There may be some contribution of anion destabilization of unbound substrate to the lowering of $K_M$, but the loss in susceptibility of HSV-1 protease to trypsin digestion in 0.8M citrate evidences a conformational change in the HSV-1 protease (FIG. 2). Hence, kosmotropes may promote a conformational state of the mature HSV-1 protease with a greater affinity for substrate than exists in a simple aqueous solution.

The effect of various salts upon activity was examined in assays where the HSV-1 protease concentration and substrate concentration were maintained constant. As shown in Table 1, many salts increase the activity of the protease, particularly those with multivalent anions. Using a fixed concentration of substrate, under the conditions described in Example 2, sodium citrate at 0.8M enhanced the observed hydrolytic rate 202-fold. Phosphate and sulfate are also potent activators of the protease, increasing activity 118- and 110-fold, respectively. Chloride has little effect, while bromide, iodide and perchlorate are all inhibitory, and are there/or not within the scope of this invention. The order of anion effectiveness for activation on a molarity basis (as opposed to ionic strength) is $Br^-$, $I^-<Cl^-<CH_3COO^-<F^-<SO_4^{2-}$, $PO_4^{2-/3-}<citrate^{3-}$. This is the same order as the Hofmeister series of anions. The activation of the HSV-1 protease by anions is relatively insensitive to stereochemical configuration, as evidenced when isocitrate was compared with citrate, or when L-malate and L-glutamate were compared with their D-isomers (Table I). The effect of the counterions on HSV protease activity was relatively insignificant, with $(NH_4)_2SO_4$ being slightly less activating relative to the $Na^+$ and $K^+$ sulfate salts.

In accordance with this invention, the stability of the protease activity in the presence or absence of various additives has been examined. The accumulation of product was linear over a 60 minute period. Hence, the wide differences in enzyme activity seen when various salts were added are not due to time-dependent differences of protease stability in the assays.

In accordance with this invention, the sensitivity of native HSV-1 protease to trypsin was examined as a function of kosmotrope concentration. Following treatment of the enzyme with trypsin for 60 minutes, SDS-PAGE was performed to qualitatively examine the extent of trypsin digestion of the HSV-1 protease. The results are shown in FIG. 2. The presence of a kosmotropic anion protected the enzyme against tryptic digestion, even though the activity of trypsin itself was shown to increase in the presence of the kosmotrope by 10%.

Another aspect of this invention is a reaction medium suitable for assays of HSV-1 protease activity which comprises a kosmotropic anion. In preferred aspects of this invention the reaction medium is aqueous, and comprises HSV-1 protease along with a kosmotropic anion selected from the group consisting of: sulfate anion, succinate anion, phosphate anion, citrate anion, isocitrate anion, aconitate anion and mixtures thereof. Preferably the anion concentration is in a range of 0.01 to 1 molar, and in more preferred embodiments, the medium comprises 0.8M sodium citrate or 0.8M sodium phosphate.

A significant aspect of this invention involving the handling and assay of HSV-1 protease is that determination of enzyme activity in the presence of a kosmotropic anion such as 0.8M sodium citrate can now be performed in minutes. In the prior art (see, for example DiIanni et al., 1993, *J. Biol Chem.* 268: 25449–25454) incubation time for an assay was hours. In this embodiment of the invention the enzyme and substrate incubate for under five minutes, and preferably for only about one minute.

In another aspect of this invention which is an improvement over the prior art is that the protease concentration in a reaction mixture containing a kosmotropic anion, such as 0.8M sodium citrate can be well below 1 micromolar. In the past (such as described by DiIanni et al., supra) HSV protease concentrations in the micromolar range have been disclosed. With substantially lower concentrations, however, such as in the nanomolar or less range, one can detect inhibitors whose dissociation constants are in the nanomolar range, which could not be done previously. In preferred embodiments, the protease concentration is as low as 40 nM.

The following non-limiting Examples are presented to better illustrate the invention.

EXAMPLE 1

Bacterial expression and enzyme purification.

A 306 amino acid precursor form of the HSV-1 protease was expressed in *E. coli* and purified with a modified version of the protocol described in Darke, P. L. et al., 1994 *J. Biol. Chem.* 269: 18708–18711, which is incorporated by reference. Briefly, soluble enzyme from lysed *E. coli* was chromatographed on E. Merck Fractogel —$SO_3$ at pH 7.0 with elution by a gradient of sodium citrate. Autoprocessing of the precursor to the mature 246 amino acid form of the enzyme was achieved by the addition of 1.8M sodium citrate to a final concentration of 0.5M to peak fractions and incubation at 4° C. for 2 hr. The processed sample was desalted on Sephadex G-25 (Pharmacia). Rechromatography on E. Merck Fractogel —$SO_3$ afforded a preparation of the mature enzyme that was greater than 95% pure as judged from sodium dodecylsulfate polyacrylamide electrophoresis (SDS-PAGE) with Coomassie brilliant blue staining. Protein concentrations were determined with quantitative amino acid analysis.

EXAMPLE 2

Cosolvent Effects

For experiments examining anion effects, buffer solutions were prepared with the sodium salt of the anion and the pH was adjusted to 7.5 with concentrated HCl where necessary (i.e., citrate, glutamate, malate). An exception was phosphate, where $NaH_2PO_4$ was prepared in the buffer and the pH adjusted upward with NaOH.

Enzyme activity was measured with the peptide substrates HTYLQASEKFKMW-amide (SEQ.ID.NO.:2) and HTYLQASEKFKMWG-amide (SEQ.ID.NO.:1), using HPLC for the separation of products from substrates as described in Darke et al., 1994, supra. The C-terminal cleavage products of enzymatic hydrolysis are SEKFKMW-amide (SEQ.ID.NO.:3) and SEKFKMWG-amide (SEQ.ID.NO.:4) respectively. Quantitation of the C-terminal cleavage product, containing tryptophan, in the HPLC effluent was with a Hewlett-Packard model 1046A fluorescence detector (excitation at 280 nm, emission at 350 nm). A 10:1 signal to noise ratio was obtained with the fluorescence detector for 45 pmol of either product. Reactions were performed at 37° C. in a pH 7.5 buffer containing 52 mM 4-morpholinoethanesulfonic acid (MES), 52 mM 3-(N-tris(hydroxymethyl)methylamino)-2-hyroxy-propanesulfonic acid (TAPSO) and 100 mM diethanolamine, 1 mM EDTA, 1 mM dithiothreitol, 0.1% bovine serum albumin, and the various additives listed in the Tables. Reactions were initiated by the addition of a stock HSV-1 protease solution (0.625 mg/ml) in the above buffer with no additives to a final concentration of 0.025 mg/ml (0.94 μM) and quenched with the addition of 5% $H_3PO_4$. Activity assays comparing various anion and cosolvents effects were conducted with a substrate concentration of 53 μM. Results for anions are shown in Table 1, below; results for co-solvents are shown in Table 2, below. Activity in Tables 1 and 2 is expressed as relative to the case where no additive was present in the reaction mixture.

TABLE I

Relative Activity of HSV-1 Protease in the Presence of Various Anions

| Anion | RELATIVE ACTIVITY | | |
|---|---|---|---|
| ($Na^+$ Salt) | 0.2M | 0.8M | Ionic strength = 0.8 |
| None | 1.00 | 1.00 | 1.00 |
| $F^-$ | 6.15 | — | — |
| $Cl^-$ | 0.96 | 1.08 | — |
| $Br^-$ | 0.23 | 0.07 | — |
| $I^-$ | 0.07 | 0.00 | — |
| $CH_3COO^-$ | 1.71 | 7.03 | — |
| $ClO_4^-$ | 0.06 | 0.00 | — |
| $SO_4^{2-}$ | 4.70 | 110. | 11.8 |
| Succinate | 3.97 | 76.5 | 6.03 |
| D-malate | 4.09 | — | — |
| L-malate | 4.04 | — | — |
| D-glutamate | 2.90 | — | — |
| L-glutamate | 2.45 | — | — |
| $HPO_4^{2-}/PO_4^{3-}$ | 5.68 | 118 | 11.8 |
| Citrate | 11.0 | 202 | 4.16 |
| Isocitrate | 7.72 | 164 | 3.53 |
| cis-Aconitrate | 5.06 | 133 | 2.40 |
| $HP_2O_7^{3-}$ | 7.32 | — | — |

TABLE 2

Relative Activity of HSV-1 Protease in the Presence of Various Co-solvents

| Co-solvent | RELATIVE ACTIVITY | | |
|---|---|---|---|
| | 2% | 5% | 10% |
| none | 1.00 | 1.00 | 1.00 |
| Dimethyl sulfoxide | 0.63 | 0.35 | 0.33 |
| Dimethyl formamide | 0.24 | 0 | 0 |
| Methanol | 0.36 | 0.15 | 0 |
| Ethanol | 0.27 | 0.10 | 0 |
| Trifluoroethanol | 0.50 | 0.15 | 0 |
| Isopropanol | 0.44 | 0.19 | 0 |
| Ethylene glycol | 0.63 | 0.67 | 0.45 |
| Glycerol | 0.85 | 1.34 | 2.48 |
| Sorbitol | 1.08 | 1.73 | 3.52 |

EXAMPLE 3

Trypsin treatment

Trypsin treatment of the HSV-1 protease (0.15 mg/ml) was performed with 0.1 mg/ml trypsin at 37° C. for 60 min. Trypsin activity s measurements with the fluorogenic substrate BOC-Val-Pro-Arg-7-amino-4-methylcoumarin were performed at 37° C. After trypsin treatment, samples were boiled with SDS gel sample buffer and small volumes of sodium citrate were added to some samples to equalize the extent of band spreading on the gel. SDS-PAGE was performed with 16% gels and proteins were visualized with coomassie brilliant blue stain.

EXAMPLE 4

Assay with Nanomolar Concentrations of HSV-1 Protease

The reaction protocol of Example 2 was followed, except that 0.8M sodium citrate was added to the reaction mixture and HSV-1 protease had a final concentration of 40 nM. The amount of peptide cleavage product (SEKFKMW-amide SEQ.ID.NO.:3) that accumulated in 60 minutes was measured by HPLC, and was found to be 100 pmol. The 100 pmol product produced a signal of greater than 20 times background noise.

EXAMPLE 5

Shortened Time Assay of HSV-1 Protease

The reaction protocol of Example 2 was followed, except that 0.8M sodium citrate was added to the reaction mixture and the enzyme concentration was 0.93 μM. The amount of peptide cleavage product (SEKFKWM-amide SEQ.ID.NO.:3) that accumulated in 1 minute was 100 pmol with a 0.93 μM final concentration of enzyme.

What is claimed is:

1. A method for increasing the activity of Herpes Simplex Virus type 1 (HSV-1) protease comprising adding a kosmotropic anion to a reaction medium containing said protease and a suitable substrate.

2. A method according to claim 1 wherein the anion is a multivalent anion.

3. A method according to claim 2 wherein the anion is selected from the group consisting of sulfate anions, succinate anions, phosphate anions, citrate anions, isocitrate anions, and aconitate anions.

4. A method according to claim 3 wherein the anion is present in a concentration of 0.01 to 1 molar.

5. A method according to claim 4 wherein the kosmotropic anion is 0.8M sodium citrate or 0.8M sodium phosphate.

6. A reaction medium suitable for assays of HSV-1 protease activity comprising HSV-1 protease, a suitable substrate and a kosmotropic anion.

7. A reaction medium according to claim 6 which is aqueous.

8. A reaction medium according to claim 7 wherein the kosmotropic anion is selected from the group consisting of sulfate anions, succinate anions, phosphate anions, citrate anions, isocitrate anions, aconitate anions, and mixtures thereof.

9. A reaction medium according to claim 8 wherein the anion is present in a concentration of 0.01 to 1 molar.

10. A reaction medium according to claim 9 wherein the kosmotropic anion is 0.8M sodium citrate or 0.8M sodium phosphate.

11. A method for assaying HSV-1 protease activity comprising:

a) preparing a reaction medium comprising HSV-1 protease, HSV-1 substrate and a kosmotropic anion; and b) measuring the resulting protease activity.

12. A method according to claim 11 wherein the reaction medium further comprises a substance suspected of altering the protease activity.

13. A method according to claim 12 wherein the protease and protease substrate are present in nanomolar amounts.

14. A method according to claim 11 wherein the assay is conducted in less than 60 minutes.

15. A method of restoring activity to HSV protease in vitro in a medium comprising HSV protease in the presence of an inactivating substance comprising contacting the protease with a kosmotropic anion.

16. Activated HSV-1 protease.

* * * * *